United States Patent [19]

Schipper

[11] Patent Number: 4,762,611

[45] Date of Patent: Aug. 9, 1988

[54] WATER QUALITY INDICATION SYSTEM

[75] Inventor: Richard A. Schipper, Leucadia, Calif.

[73] Assignee: Myron L Company, Inc., Carlsbad, Calif.

[21] Appl. No.: 97,050

[22] Filed: Sep. 16, 1987

[51] Int. Cl.⁴ .............................................. B01D 35/14
[52] U.S. Cl. ..................................... 210/85; 210/96.2; 222/40
[58] Field of Search ..................... 73/53; 210/85, 96.2; 222/40

[56] References Cited

U.S. PATENT DOCUMENTS

| | | | |
|---|---|---|---|
| 2,987,187 | 6/1961 | Comroe | 210/96.1 X |
| 3,252,578 | 5/1966 | Smith et al. | 210/96.1 X |
| 3,276,458 | 10/1966 | Iversen et al. | 210/85 X |
| 3,512,643 | 5/1970 | Forss | 210/96.1 |
| 3,578,164 | 5/1971 | Weiss et al. | 210/96.1 |
| 3,774,763 | 11/1973 | Yall et al. | 210/96.2 |
| 3,838,774 | 10/1974 | Dolan et al. | 210/85 |
| 3,841,483 | 10/1974 | Overton | 210/96.1 X |
| 3,856,676 | 12/1974 | Grimme, Jr. et al. | 210/96.1 |
| 3,973,572 | 8/1976 | Brous | 210/96.1 X |
| 3,990,066 | 11/1976 | Malmgren | 210/85 X |
| 4,563,272 | 1/1986 | Yoshida et al. | 210/96.1 X |
| 4,622,133 | 11/1986 | Furuno | 210/96.1 X |
| 4,683,054 | 7/1987 | Turnbull | 210/96.1 X |

FOREIGN PATENT DOCUMENTS

| | | | |
|---|---|---|---|
| 2626572 | 12/1977 | Fed. Rep. of Germany | 210/85 |
| 136487 | 6/1986 | Japan | 210/85 |

Primary Examiner—Robert Spitzer

[57] ABSTRACT

A water conductivity sensing and indicating system arranged for association with a water faucet and maintainable water processing apparatus includes apparatus for indicating whether the water conductivity exceeds or is less than some predetermined conductivity level. It also includes apparatus in the form of one or both of a flow actuated switch and a liquid crystal display for limiting battery power consumption to the end that minimum sized batteries need not be replaced oftener than the processing unit need be maintained.

12 Claims, 2 Drawing Sheets

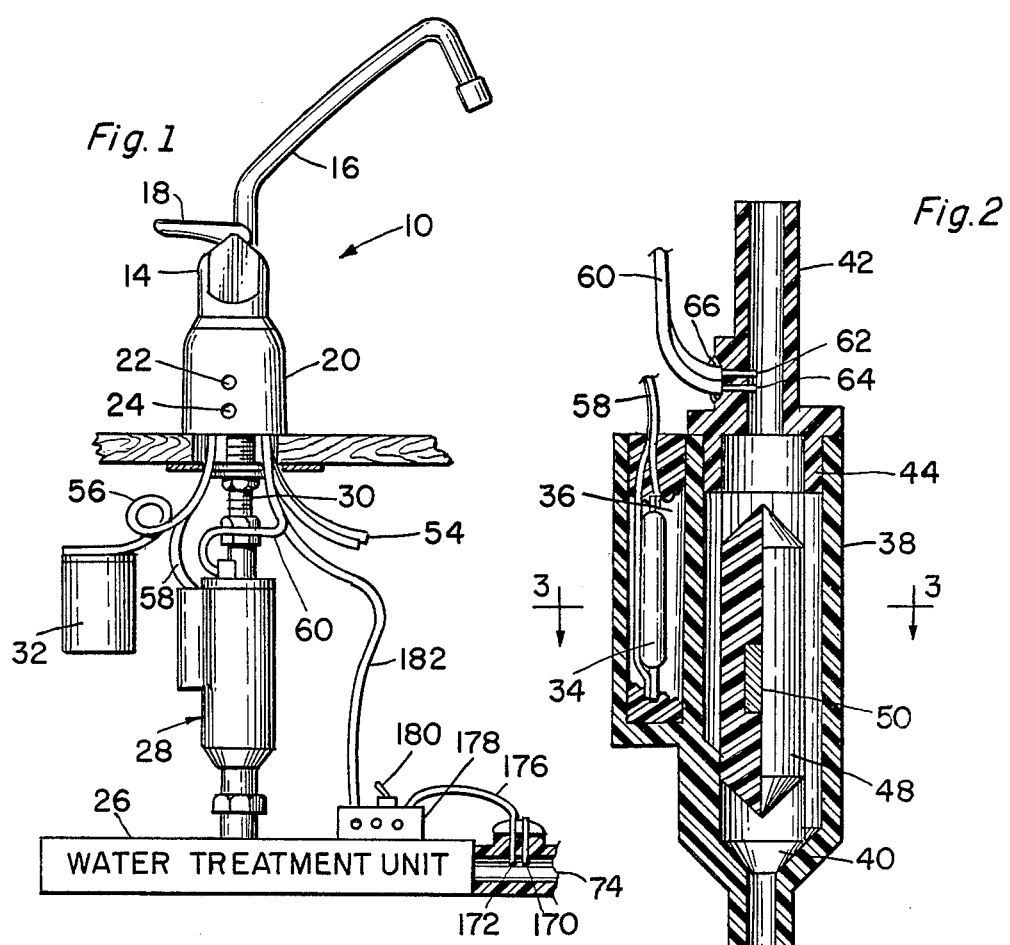

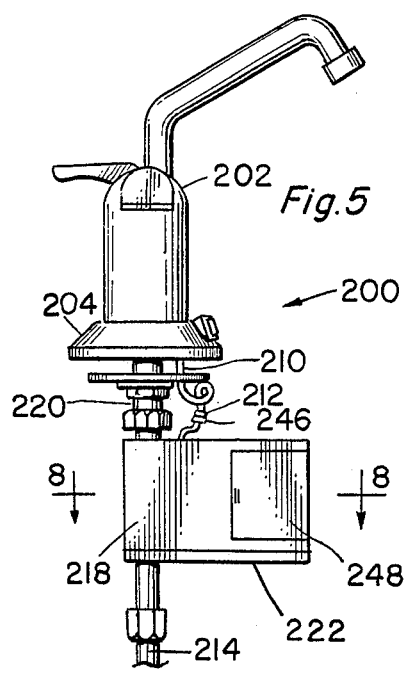
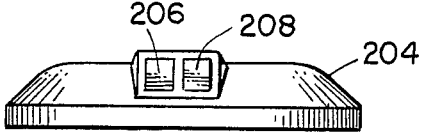
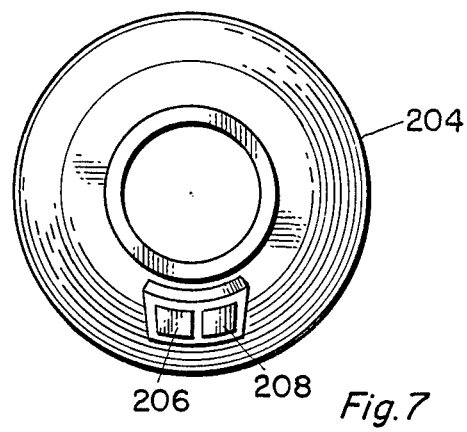
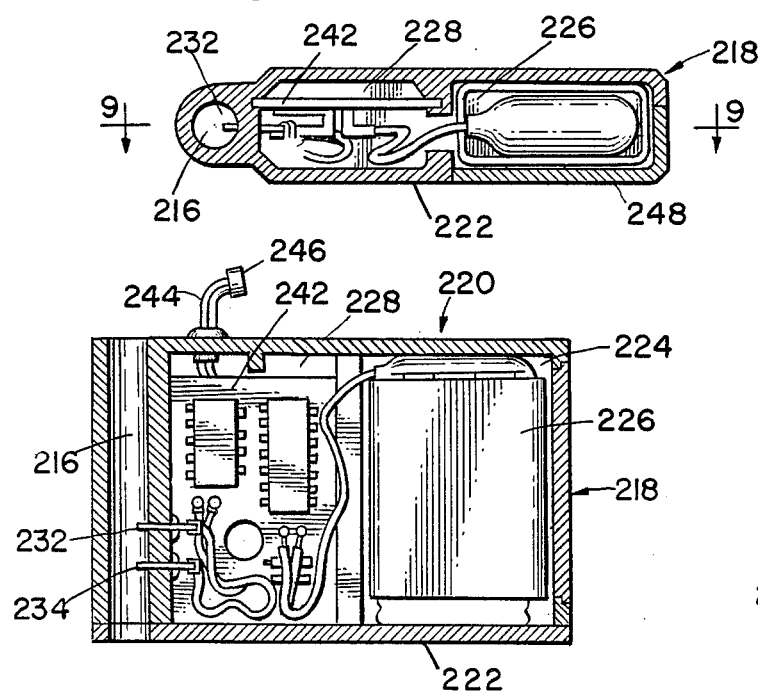
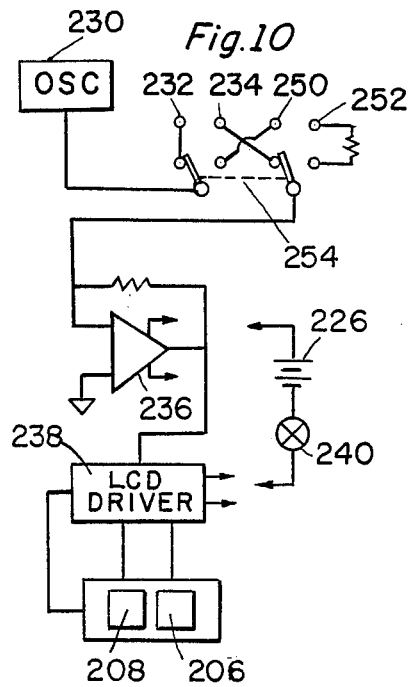

WATER QUALITY INDICATION SYSTEM

This invention relates to systems for measuring and indicating whether the conductivity of water is less or greater than some predetermined amount.

BACKGROUND

The reverse osmosis phenomenon is widely used in under-the-sink apparatus for making "purified" drinking water available at a faucet mounted on the sink top. The process is practiced with the aid of a membrane whose usefulness is limited and which must be replaced from time to time. The need for replacement is a function of the history of impurity removal rather than time or taste. However, in the absence of a means for measuring that history or of measuring taste it is common for manufacturers of reverse osmosis machines to recommend changing membranes periodically. In practice the time interval between change is so long that the time for change is easily forgotten or the need for service has itself been forgotten. The result in such cases is that membranes are changed more often than needed or not often enough.

In the case of drinking water "purification", the permissible magnitude of impurity content is established arbitrarily. In the case of water supplied by municipal or commercial organization, the value ordinarily is set by the purification system manufacturer or by the installer at some value less than the water supplier's maximum content standard.

Total impurity content is difficult to measure but finding the content of electrically conductive material in relative terms is not. It is common to measure water purity as a function of the electrical conductance between a pair of electrodes spaced a fixed distance apart while immersed in the water to be evaluated. While the measurement is easy to make with a simple conductivity meter, power is required to make and display the measurement. If the user must remember to apply that power and to make the measurement periodically, little has been gained and the opportunity for failure to detect when a membrane change is to be made is as great as in the past. An alternative is to apply power continually and to provide a continuous indication of the water's conductivity. To do that raises other problems. Continuous indication may require so much power that using batteries as the power source may be impractical. On the other hand, to employ alternating "house" current requires rectification and current control and safety measures which are generally cost prohibitive. One solution has been to employ battery power and an intermittent indication and display. It is the purpose of this invention to provide better solutions to the problem.

SUMMARY

It is an object of this invention to provide a system for indicating whether the conductivity of drinking water exceeds a preselected level of conductivity.

Another object is to provide a water conductivity measuring and indicating system which may be powered with an inexpensive, readily available battery the service life of which will greatly exceed the service life of currently used purification membranes.

Another object is to provide such a system which is powered and operative to measure and indicate only when water is being drawn at the faucet.

A further object is to prove such a system which is operative to measure the effectiveness of the associated water treatment apparatus.

These and other objects and advantages of the invention are realized in part by the provision of the combination of:

a water faucet having a base;

indicating means carried by said base and responsive to electrical signals for indicating whether the conductivity of water being delivered to said faucet is less than a preselected water conductivity;

sensing means responsive to the electrical conductance of water for generating electrical signals indicative of water conductivity; and power consumption limiting means for limiting power consumption by said display means comprising at least one of a liquid crystal display incorporated in said indicating means and a water flow responsive switch.

The Drawings

In the Drawings:

FIG. 1 is an elevational view, partly sectioned, of the pertinent parts of a preferred system according to the invention;

FIG. 2 is a view in central cross-section of the switch and switch actuator portion of the apparatus of FIG. 1;

FIG. 3 is a cross-sectional view of the apparatus of FIG. 1 taken on line 3—3 of FIG. 2;

FIG. 4 is a diagram of an electronic circuit employed in the invention;

FIG. 5 is an elevational view of the pertinent parts of an alternative preferred embodiment of the invention;

FIG. 6 is an elevational view of the display section of the apparatus of FIG. 1;

FIG. 7 is a top plan view of the display section;

FIG. 8 is a cross-sectional view taken on line 8—8 of FIG. 5;

FIG. 9 is a cross-sectional view taken on line 9—9 of FIG. 8, and

FIG. 10 is a block diagram of the electrical measuring and indicating circuit which is incorporated in the apparatus of FIGS. 5 through 9.

DESCRIPTION OF PREFERRED EMBODIMENTS

FIGS. 1 through 4 show a water conductivity measuring and indicating system which is powered and operative only while the water to be measured is flowing. FIGS. 5 through 10 illustrate a system utilizing a liquid crystal display in which measurement and display are continuous. A third embodiment, which will be described by reference to all of the Figures, uses components of the first and second described systems to provide liquid display indication only while the water to be measured is flowing.

THE EMBODIMENT OF FIGS. 1 THROUGH 4

In FIG. 1 the system 10 includes a water faucet 12 the components of which are a valve 14, an outlet spout 16 and a valve actuating handle 18. The faucet is mounted atop an indicating base 20 in whose wall two light emitting diodes, a yellow or red one 22 and a green one 24, are fixed such as to be visible from the exterior of the base. Water from a pressurized source, not shown, flows to the valve through the series combination of a supply conduit 26, a water flow sensor 28 and a connecting conduit 30. Electrical power for the measurement and display circuitry is provided by a battery 32 which in this case is a nine volt "NEDA 1604" type unit. The circuitry is potted and mounted in the base 20.

In FIG. 4 the battery 32 is shown to be connected in series with an on-off switch 34. In this embodiment, that switch is an enclosed, magnetically actuated reed switch. It is visible in FIGS. 2 and 3 where it is shown to be housed in a cavity 36 formed in the main body 38 of the flow sensor 28. Cavity 36 is separate from but extends parallel to the cavity 40 which in combination with housing extension 42 forms a flowpath for water from water treatment unit 26 to connecting conduit 30. The housing extension 42 is bonded to the upper end of the main body 38 with it's downwardly extending cylindrical extension 44 press fitted into the upper end of cavity 40. The latter opens to a smaller diameter inlet passage 46 at it's lower end. A movable plug 48 is disposed in the cavity 40. It contains a magnet 50 embedded centrally within it which is capable of actuating the reed switch when in juxtaposition therewith. Longitudinal guide ribs 52 extend inwardly from the interior wall of cavity 40. They guide and permit reciprocal motion of the plug from a lower position in which the reed switch is not actuated to an upper position in which the plug's magnet causes closure of the reed switch. The plug is shaped such that the pressure of water flowing upwardly through the flow sensor housing past the plug forces the plug to switch actuating position. When flow ceases the plug drops below that position. Thus in FIG. 4 the electronic circuitry is energized only while water is flowing past the plug.

In FIG. 1 the lines 54 are water return lines related to an air gap which is required in some political jurisdictions to be included in the water flow circuit. They are not related to the invention except in the sense that the invention imposes no limits on that feature. Lines 56 and 58 connect the battery 32 and the switch 34, respectively, to the remainder of the circuitry. Lines 60 connect that circuitry to a pair of electrodes 62 and 64 which extend into the water flowpath. In this embodiment they are located at a point in the flow sensor housing member 42. The electrodes are visible in FIG. 2. They are fixed in place in a lateral extension of the housing member 42 with an adhesive plug 66. In similar fashion the switch 34 and the lead wires 58 are fixed in place, and cavity 36 is closed, by quantities of an adhesive. In FIG. 4 the battery 32 and switch 34 are connected in series across positive line 68 and negative line 70. The positive and negative terminals of each section of a two section operational amplifier package LM1458 are connected across those lines, respectively. The positive input of section 72 is connected to line 68 through a resistor 74, to negative line 70 through a resistor 76 and to it's output terminal through a feedback resistor 78. The negative input of section 72 is connected to the negative line through a capacitor 80 and to the device's output terminal through feedback resistor 82. In addition, the output terminal of device 72 is connected to electrode 62 and to one side of a set 84 of four resistors connected in parallel. The other side of the set is connected through a diode 86 to the positive input of the other operational amplifier section 88 and through a feedback resistor 90 to the output of section 88. In addition, said other side of the resistor network is connected through resistor 92 to the junction between the resistor and capacitor of a series circuit which extends from electrode 64 through the resistor 94 and capacitor 96 to negative line 70. Terminal 64 is also connected to the negative input of device 88 through diode 98. The positive and negative inputs of device 88 are connected to line 70 through capacitors 100 and 102, respectively. The output of device 88 is connected to the junction of diodes 104 and 106 of a circuit which extends from positive line 68 through the series combination of limiting resistor 108, green light emitting diode 24, diode 104, the junction point, diode 106 and red or yellow light emitting diode 22 and a current limiting resistor 114 to negative line 70.

The device 72 operates as an oscillator which delivers power continuously to the terminal 62 and to the left side of parallel resistor network 84 as an alternating current. The device 88 is connected as a differential amplifier. It compares the potential at the right side of the resistor network 84 with the potential at electrode 64. In effect the device compares the conductance of the network 84 to the conductance from terminal 62 to terminal 64. The conductance between those terminals is determined in operation by the conductivity of the water in which the terminals are immersed which, in turn, is determined by the amount of dissolved material in the water. When the conductivity through the water is low and the conductance across the terminals 62 and 64 is lower than the conductance of network 84, the output of device 88 is negative. Current flows from the device to positive line 68 and the green diode 24 is illuminated. Conversely, if the amount of dissolved impurities is high, the conductance across terminals 62 and 64 will rise above that of network 84 and the output of device will be positive. In that circumstance it is the red or yellow diode 22 which will be illuminated. Neither diode is illuminated when the faucet is closed because in that case the switch 34 will have opened. In this embodiment the resistor network is arranged so that the connecting leads of certain of the resistors are readily cut. Cutting leads increases the conductivity of the network and has the effect of increasing the level of impurities at which the output indication changes from green to red or yellow.

The use of electrical energy is limited to the times when the faucet is open and water runs.

For convenience in servicing of the water treatment unit, a means is provided by which a service person, and the user, can assess the effectiveness of the water treatment unit. In the case of a reverse osmosis machine this means permits a determination of the effectiveness of the filtration membrane. In FIG. 1, a second pair of test electrodes 170 and 172 are exposed to the supply water in the supply conduit by which water is supplied to the water treatment unit 26. Those electrodes are connected by cable 176 to a junction box 178 which is associated with the water treatment unit. The junction box includes a single pole, single throw switch 180 and three test jacks. A cable 182 connects the junction box to the circuitry housed in base 20.

In the circuit of FIG. 4 the test jacks are numbered 184, 186 and 188. Jack 184 is connected to the output of device 72 and to each of electrodes 60 and 170. Jack 186 is connected to electrode 172 and jack 188 is connected to electrode 64. The common terminal of switch 180 is connected to diode 86. One of the switched terminals of the switch, the normally closed terminal, is connected to the resistor network 84. The other switched terminal, the test terminal, is connected to electrode 172 through a calibrating resistor 190.

The operation of the unit when the switch 180 is in normal position has been described. In test position, the unit compares the conductance across electrodes 62 and 64 with the sum of the conductance across resistor 190 and the electrodes 170 and 172. Resistor 190 is chosen so that the combination of it's conductance and that of the supply water as measured at electrodes 170 and 172 is greater than the conductance of the product water across electrodes 62 and 64 when the conductance of the product water is a selected amount higher, such as 70 percent higher than the conductance of the supply water. As the treatment unit becomes less effective to remove dissolved impurities, the difference in water conductance lessens. When the difference is small enough, the voltage at the negative input of device 88 will become greater than the voltage at the positive input and the display will change from green to red or yellow. The service man can determine and compare the actual conductance of the water before and after processing by connecting a conductivity meter between the test jack 184 and each of jacks 186 and 188.

THE EMBODIMENT OF FIGS. 5 THROUGH 10

The system 200 of FIG. 5 includes a faucet 202 which is similar to the faucet 12 of FIG. 1. The base 204 is shaped differently. It serves as a trim member and it serves as the housing for a two pixel liquid crystal display unit. The individual liquid crystal display areas or pixels 206 and 208. In this embodiment the electronic circuitry is packaged in a housing that is positioned below the sink top rather than in the base 204. Lead wires 210 are connected at one end to the liquid crystal display units 206 and 208 and are connected at the opposite end to a plug 212. Water flows to the faucet from a reverse osmosis or other water treatment apparatus which is connected to the supply conduit 214. From there it flows through the series combination of the flowpath 216 in the flowpath and sensor housing 218 and a connecting conduit 220 to the faucet 202. The housing 218 is shown in cross-section in FIGS. 8 and 9. In addition to it's flowpath, which is just a straight, cylindrical passage formed therethrough, the housing has a portion 222 which extends laterally from the mid-region of its length. Portion 222 defines two cavities. One is numbered 224. It houses the battery 226. The other cavity 228 houses electronic circuitry which is connected to the battery 226, the plug 212 and to a pair of spaced electrodes which are embedded in the housing and extend from ends exposed in the flowpath 216 to opposite ends which extend into cavity 228.

The circuit is shown in FIG. 10. It is formed of standard, commercially available units shown here in block form. The liquid display units are opaque and black when not energized. They become transparent when energized. Only one display unit is required to indicate an impurity level above the maximum impurity standard. Thus only one indicator would be included if additional power limitation is desired. In this embodiment one or the other of the displays 206 and 208 is energized and the other is not. The rear surface of display 206 is colored green and the rear surface of display 208 is colored red, or yellow if preferred. If desired the colored overlay may bear a trademark or color may be omitted in favor of some other legend or symbol which indicates quality level. When display 206 is energized, it appears to be green and when display 208 is energized, it appears to be red, or yellow.

In FIG. 10 the output of oscillator 230 is normally applied to the electrode 232. The other electrode 234 is connected to the positive input of an operational amplifier 236 whose other input is connected to negative ground. The output of the amplifier 236 is applied to a polarity sensitive decoder 238 called an LCD DRIVER or liquid crystal driver. The driver output is applied to one or the other of displays 206 and 208. The elements other than the battery, electrodes and the optional flow responsive switch 240 are mounted on circuit board 242 in the cavity 228. A cable 244 extends from the circuit board to a socket 246 which is mated at the time of installation with the plug 212. In this model the housing has an opening which affords easy access to the battery and is closed by a cover 248.

Like the circuit of FIG. 4, this one includes a pair of test electrodes 250 and 252 which are exposed to supply water upstream from the water processing unit. A switch, this time a double pole, double throw switch 254 permits selection of one air of the test electrodes or the other. Test jacks are not shown but may be included if desired.

A third embodiment adds the flow sensing switch of FIGS. 1 through 4 and connects it in series with battery 226 in the embodiment of FIGS. 5 through 10. The effect is to disable the sensing and display function until the faucet is opened and the reed switch is actuated by lifting of the plug and it's magnet. In ordinary household use the power consumption of the liquid display is so small that the battery will last longer than the interval between membrane changes so the expense of the flow actuated switch is not warranted in most cases. None-the-less the third embodiment has applications.

I claim:

1. A water conductivity sensor and indicating system comprising in combination:
   a water faucet having a base;
   indicating means carried by said base and responsive to electrical signals for indicating whether the conductivity of water being delivered to said faucet is less than a preselected water conductivity;
   sensing means responsive to the electrical conductance of water for generating electrical signals indicative of water conductivity; and
   power consumption limiting means for limiting power consumption by said display means comprising at least one of a liquid crystal display incorporated in said indicating means and a water flow responsive switch.

2. The invention defined in claim 1 in which said electrical signals generated by said sensing means are intermittent.

3. The invention defined in claim 1 in which said indicating means comprises a two color display responsive to said electrical signals to display one or the other of said colors at a time.

4. The invention defined in claim 1 in which said power consumption limiting means comprises a water flow responsive switch in the form of magnet whose position is altered as a function of water flow and a magnetically actuated switch responsive to the position of said magnet.

5. The invention defined in claim 4 in which said system comprises a housing having a flow path for water formed therethrough a portion of the length of which flowpath defines a first cavity, the housing having a second cavity formed therein proximate to said first cavity;
   said magnet being disposed in said first cavity and said switch being disposed in said second cavity.

6. A water conductivity sensor and indicating system comprising in combination:
- indicating means responsive to electrical signals for indicating when the conductivity of water being delivered to a faucet is less than a preselected water conductivity;
- sensing means responsive to the electrical conductance of water for generating electrical signals indicative of water conductivity; and
- power consumption limiting means for limiting power consumption by said display means comprising a liquid crystal display incorporated in said indicating means.

7. The invention defined in claim 6 in which further comprises an indicia bearing element which is visible to a user only when said liquid crystal display is energized.

8. The invention defined in claim 7 in which said indicia bearing element is a colored element.

9. The invention defined in claim 6 in which said indicating means further comprises means for indicating when the conductivity of water being delivered exceeds a preselected water conductivity.

10. The invention defined in claim 9 in which said indicating means includes two conductivity level indicia bearing elements one of which is rendered visible when the conductivity of delivered water is less than some predetermined conductivity and is rendered invisible when the conductivity of delivered water exceed some given predetermined conductivity.

11. A water conductivity sensor and indicating system for use in an installation in which supply water is delivered to a water processing unit and from the water processing unit to a faucet, the system comprising in combination:
- indicating means responsive to electrical signals for indicating when the conductivity of water being delivered to said faucet is less than a preselected water conductivity or is less than a selected amount greater than the conductivity of said supply water;
- sensing means responsive to the electrical conductance of water for generating first electrical signals indicative of the conductivity of water being delivered to said faucet;
- Sensing means responsive to a selected one of a predetermined conductance and of the supply water for generating second electrical signals indicative of the conductivity of the selected one of said supply water and said predetermined conductance; and
- means for applying said first and second electrical signal to said indicating means.

12. The invention defined in claim 11 which further comprises power consumption limiting means for limiting power consumption by said display means comprising a liquid crystal display incorporated in said indicating means.

* * * * *